(12) United States Patent
Crawford et al.

(10) Patent No.: US 9,480,516 B2
(45) Date of Patent: Nov. 1, 2016

(54) PERCUTANEOUS BONE SCREW DEVICE AND METHOD

(71) Applicants: GLOBUS MEDICAL, INC., Audubon, PA (US); EXCELSIUS SURGICAL, L.L.C., Phoenix, AZ (US)

(72) Inventors: Neil R. Crawford, Chandler, AZ (US); Nicholas Theodore, Paradise Valley, AZ (US); Mitchell A. Foster, Scottsdale, AZ (US)

(73) Assignee: Globus Medical, Inc., Audubon, PA (US)

( * ) Notice: Subject to any disclaimer, the term of this patent is extended or adjusted under 35 U.S.C. 154(b) by 272 days.

(21) Appl. No.: 14/021,846

(22) Filed: Sep. 9, 2013

(65) Prior Publication Data

US 2015/0073487 A1    Mar. 12, 2015

(51) Int. Cl.
*A61B 17/86* (2006.01)
*A61B 17/00* (2006.01)
*A61B 17/70* (2006.01)
*A61B 17/88* (2006.01)

(52) U.S. Cl.
CPC ......... *A61B 17/8635* (2013.01); *A61B 17/865* (2013.01); *A61B 17/866* (2013.01); *A61B 17/7032* (2013.01); *A61B 17/888* (2013.01); *A61B 2017/00336* (2013.01); *A61B 2017/00893* (2013.01)

(58) Field of Classification Search
CPC .......... A61B 17/7032; A61B 17/7034; A61B 17/7076; A61B 17/708; A61B 17/7082; A61B 17/84; A61B 17/86; A61B 17/8605; A61B 17/861; A61B 17/8615; A61B 17/862; A61B 17/8625; A61B 17/863; A61B 17/8635; A61B 17/865; A61B 2017/00336; A61B 2017/0089; A61B 2017/00893; A61B 2017/8655; A61B 2019/4805; A61B 2019/481
USPC .................................. 606/300–321
See application file for complete search history.

(56) References Cited

U.S. PATENT DOCUMENTS 4,154,342 A * 5/1979 Wallace .................. A61L 2/022
                                                  206/439
4,712,681 A * 12/1987 Branemark ........... A61F 2/0095
                                                  206/438

(Continued)

FOREIGN PATENT DOCUMENTS

WO    WO-2011/115738    * 9/2011

*Primary Examiner* — Christian Sevilla
*Assistant Examiner* — Eric S Gibson

(57) ABSTRACT

Embodiments of the invention provide a bone screw device including a bone screw with a temporary encasement. In some embodiments, the temporary encasement comprises a biocompatible material that may be an osteoinductive, a hemostatic and or a bacteriocide. Some embodiments include a temporary encasement including a therapeutic. In some embodiments, the temporary encasement comprises a wax. In some embodiments, the screw head is substantially U-shaped. In some embodiments, the screw includes an extension tip extending from the screw shaft. Some embodiments of the invention include a system for percutaneous implantation of a bone screw including a screwdriver shaft rotatably coupled to a screw that includes a temporary encasement. In some embodiments, the screw shaft can be at least partially rotated by the screwdriver shaft. Some further embodiments further include a retractable sleeve at least partially surrounding the screwdriver shaft and the bone screw.

20 Claims, 5 Drawing Sheets

(56) References Cited

U.S. PATENT DOCUMENTS

| | | | | |
|---|---|---|---|---|
| 5,122,132 A * | | 6/1992 | Bremer | A61B 17/8635 411/386 |
| 5,458,642 A * | | 10/1995 | Beer | A61F 2/4425 606/247 |
| 5,505,736 A * | | 4/1996 | Reimels | A61B 17/86 606/318 |
| 5,713,901 A * | | 2/1998 | Tock | A61B 17/72 606/151 |
| 6,159,210 A * | | 12/2000 | Voor | A61B 17/6433 606/56 |
| 6,328,746 B1 * | | 12/2001 | Gambale | A61B 17/8625 606/104 |
| 6,656,213 B2 * | | 12/2003 | Solem | A61F 2/95 606/108 |
| 6,689,125 B1 * | | 2/2004 | Keith | A61B 17/0401 606/32 |
| 7,650,991 B2 * | | 1/2010 | Hester | B25B 23/00 206/339 |
| 7,766,920 B2 * | | 8/2010 | Ciccone | A61B 17/1615 606/104 |
| 7,909,249 B2 * | | 3/2011 | Bagozzi | A61B 19/026 235/375 |
| 8,048,129 B2 * | | 11/2011 | Forton | A61B 17/1655 606/252 |
| 8,087,325 B2 * | | 1/2012 | Neubardt | A61B 17/8875 206/347 |
| 8,241,340 B2 * | | 8/2012 | Froehlich | A61B 17/7097 606/300 |
| 8,282,651 B2 * | | 10/2012 | Ciccone | A61B 17/1615 606/104 |
| 8,292,174 B2 * | | 10/2012 | Bagozzi | A61B 19/026 235/375 |
| 8,323,293 B2 * | | 12/2012 | Morgan | A61B 17/0401 227/119 |
| 8,382,840 B2 * | | 2/2013 | Hestad | A61F 2/4611 606/86 A |
| 8,414,628 B2 * | | 4/2013 | Melkent | A61B 17/7001 606/264 |
| 8,460,306 B2 * | | 6/2013 | Schaffran | A61C 8/0089 606/104 |
| 8,708,885 B2 * | | 4/2014 | Khamis | A61B 17/00234 600/37 |
| 8,770,460 B2 * | | 7/2014 | Belzer | A61B 17/115 227/179.1 |
| 2002/0016594 A1 * | | 2/2002 | Schlapfer | A61B 17/863 606/308 |
| 2002/0045940 A1 * | | 4/2002 | Giannetti | A61F 2/30756 623/11.11 |
| 2002/0077653 A1 * | | 6/2002 | Hudson | A61B 17/0057 606/192 |
| 2002/0095214 A1 * | | 7/2002 | Hyde, Jr. | A61B 17/1604 623/18.12 |
| 2003/0028178 A1 * | | 2/2003 | Chin | A61B 19/081 606/1 |
| 2003/0187445 A1 * | | 10/2003 | Keith | A61B 17/0401 623/17.11 |
| 2004/0049283 A1 * | | 3/2004 | Patel | A61F 2/441 623/17.16 |
| 2005/0012617 A1 * | | 1/2005 | DiSilvestro | A61F 2/32 340/572.8 |
| 2005/0059864 A1 * | | 3/2005 | Fromovich | A61B 19/24 600/201 |
| 2005/0131408 A1 * | | 6/2005 | Sicvol | A61B 17/7091 606/86 A |
| 2005/0149031 A1 * | | 7/2005 | Ciccone | A61B 17/1615 606/280 |
| 2005/0154390 A1 * | | 7/2005 | Biedermann | A61B 17/7035 128/898 |
| 2005/0215862 A1 * | | 9/2005 | Larson | A61B 1/32 600/201 |
| 2005/0261691 A1 * | | 11/2005 | Hester | B25B 23/00 222/307 |
| 2006/0069391 A1 * | | 3/2006 | Jackson | A61B 17/7037 606/62 |
| 2006/0129225 A1 * | | 6/2006 | Kopia | A61B 17/115 623/1.13 |
| 2006/0167454 A1 * | | 7/2006 | Ludwig | A61B 17/7088 606/86 A |
| 2006/0224242 A1 * | | 10/2006 | Swords | A61B 17/8085 623/17.19 |
| 2006/0243616 A1 * | | 11/2006 | Caron | A61B 19/026 206/349 |
| 2006/0271094 A1 * | | 11/2006 | Hudson | A61B 17/0057 606/196 |
| 2007/0118157 A1 * | | 5/2007 | Zuidema | A61B 19/087 606/153 |
| 2007/0162029 A1 * | | 7/2007 | Whitmore | A61B 17/863 606/308 |
| 2007/0270842 A1 * | | 11/2007 | Bankoski | A61B 17/7076 606/86 A |
| 2008/0082103 A1 * | | 4/2008 | Hutton | A61B 17/7004 606/272 |
| 2008/0177335 A1 * | | 7/2008 | Melkent | A61B 17/7001 606/309 |
| 2008/0221623 A1 * | | 9/2008 | Gooch | A61B 17/686 606/302 |
| 2008/0221681 A1 * | | 9/2008 | Trieu | A61B 17/866 623/11.11 |
| 2008/0230423 A1 * | | 9/2008 | Loeffler | A61B 17/865 206/438 |
| 2008/0255621 A1 * | | 10/2008 | Fricker | A61B 17/685 606/302 |
| 2009/0048601 A1 * | | 2/2009 | Forton | A61B 17/1655 606/246 |
| 2009/0048675 A1 * | | 2/2009 | Bhatnagar | A61B 17/0642 623/17.16 |
| 2009/0192552 A1 * | | 7/2009 | Andersen | A61B 17/8685 606/302 |
| 2009/0198291 A1 * | | 8/2009 | Kevin | A61B 17/8635 606/305 |
| 2009/0204108 A1 * | | 8/2009 | Steffen | A61B 17/068 606/1 |
| 2009/0266728 A1 * | | 10/2009 | Turner | A61B 17/865 206/363 |
| 2009/0266890 A1 * | | 10/2009 | Bagozzi | A61B 19/026 235/385 |
| 2009/0275994 A1 * | | 11/2009 | Phan | A61B 17/7064 606/86 A |
| 2010/0048990 A1 * | | 2/2010 | Bakos | A61B 17/3478 600/106 |
| 2010/0114097 A1 * | | 5/2010 | Siravo | A61B 17/686 606/62 |
| 2010/0160968 A1 * | | 6/2010 | Joshi | A61B 17/7026 606/263 |
| 2010/0163598 A1 * | | 7/2010 | Belzer | A61B 17/115 227/181.1 |
| 2010/0204802 A1 * | | 8/2010 | Wilson | A61B 5/0031 623/23.6 |
| 2010/0268242 A1 * | | 10/2010 | Ciccone | A61B 17/1615 606/104 |
| 2010/0274074 A1 * | | 10/2010 | Khamis | A61B 17/00234 600/37 |
| 2010/0286703 A1 * | | 11/2010 | Morgan | A61B 17/0401 606/99 |
| 2010/0331852 A1 * | | 12/2010 | Neubardt | B25B 23/06 606/104 |
| 2011/0114514 A1 * | | 5/2011 | Bagozzi | A61B 19/026 206/216 |
| 2011/0114699 A1 * | | 5/2011 | Baxter, III | A61B 17/115 227/175.1 |
| 2011/0118761 A1 * | | 5/2011 | Baxter, III | A61B 1/00087 606/148 |
| 2011/0163147 A1 * | | 7/2011 | Laurent | A61B 17/072 227/175.2 |
| 2011/0313460 A1 * | | 12/2011 | McLean | A61B 17/7011 606/264 |
| 2012/0136398 A1 * | | 5/2012 | Mobasser | A61B 17/8635 606/311 |
| 2012/0181200 A1 * | | 7/2012 | Hulliger | A61B 19/0256 206/438 |
| 2012/0209321 A1 * | | 8/2012 | Yassinzadeh | A61B 17/0057 606/213 |

(56) References Cited

U.S. PATENT DOCUMENTS

| | | | |
|---|---|---|---|
| 2013/0012954 A1* | 1/2013 | Paroth | A61B 17/7037 606/104 |
| 2013/0012955 A1* | 1/2013 | Lin | A61B 17/1671 606/104 |
| 2013/0053847 A1* | 2/2013 | Siravo | A61B 17/7241 606/62 |
| 2013/0103094 A1* | 4/2013 | Beale | A61B 17/7076 606/279 |
| 2013/0165981 A1* | 6/2013 | Clasbrummel | A61B 17/8033 606/289 |
| 2013/0226025 A1* | 8/2013 | Bourlion | A61B 5/6878 600/547 |
| 2013/0226239 A1* | 8/2013 | Altarac | A61B 17/7064 606/247 |
| 2013/0253595 A1* | 9/2013 | Zucherman | A61B 17/8625 606/305 |
| 2014/0025124 A1* | 1/2014 | Champagne | A61B 17/863 606/308 |
| 2014/0039567 A1* | 2/2014 | Hoefer | A61B 17/708 606/86 A |
| 2014/0058460 A1* | 2/2014 | Reed | A61B 17/8625 606/312 |
| 2014/0174971 A1* | 6/2014 | Lindner | A61F 2/0095 206/438 |
| 2014/0180298 A1* | 6/2014 | Stevenson | A61B 17/7082 606/104 |
| 2014/0277139 A1* | 9/2014 | Vrionis | A61F 2/4455 606/246 |
| 2014/0277188 A1* | 9/2014 | Poulos | A61B 17/1655 606/304 |
| 2014/0324062 A1* | 10/2014 | Heuer | A61B 17/7082 606/104 |
| 2014/0371756 A1* | 12/2014 | Marigowda | A61B 17/7082 606/104 |
| 2015/0045769 A1* | 2/2015 | Cabrera Aquino | A61D 7/00 604/506 |
| 2015/0073487 A1* | 3/2015 | Crawford | A61B 17/8635 606/302 |
| 2015/0105796 A1* | 4/2015 | Grace | A61B 17/320016 606/129 |
| 2015/0164530 A1* | 6/2015 | Carver | A61B 17/32053 606/129 |

* cited by examiner

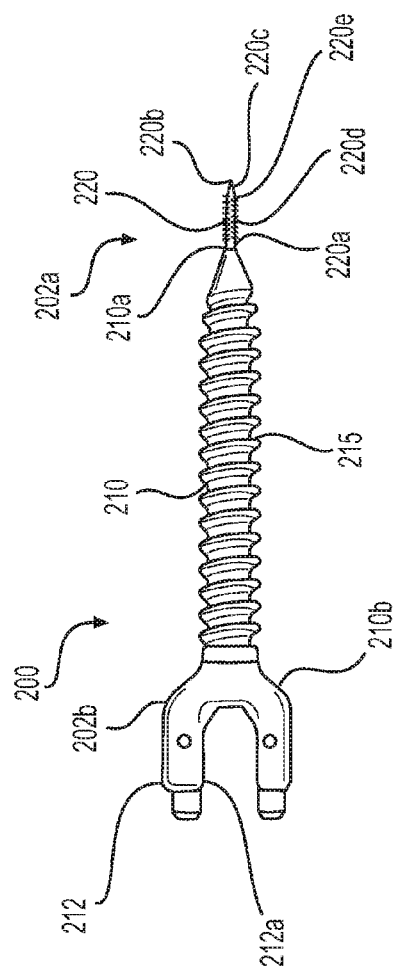
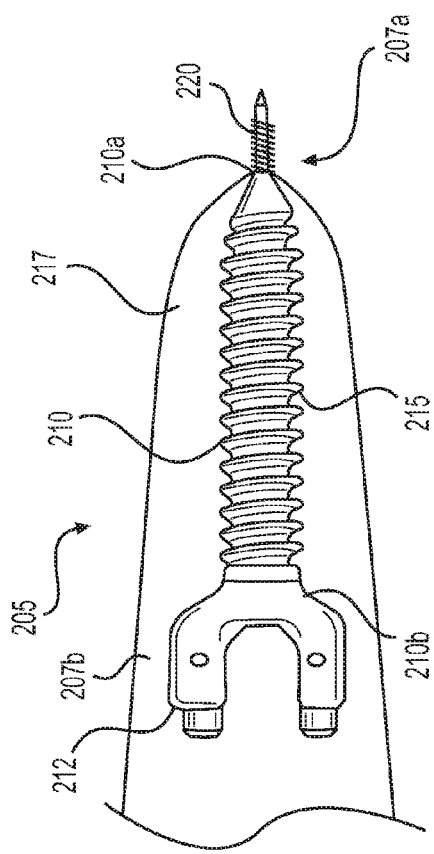

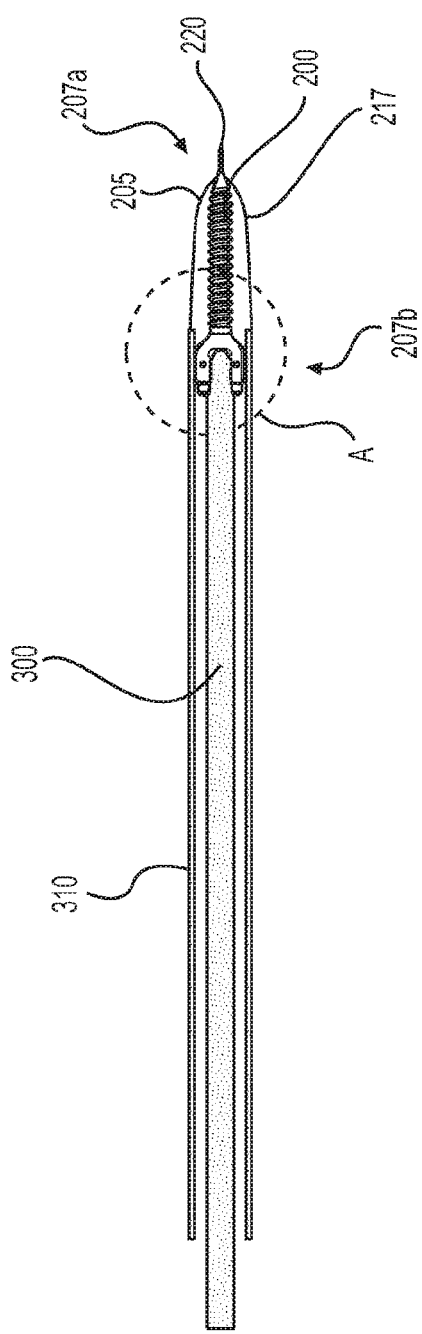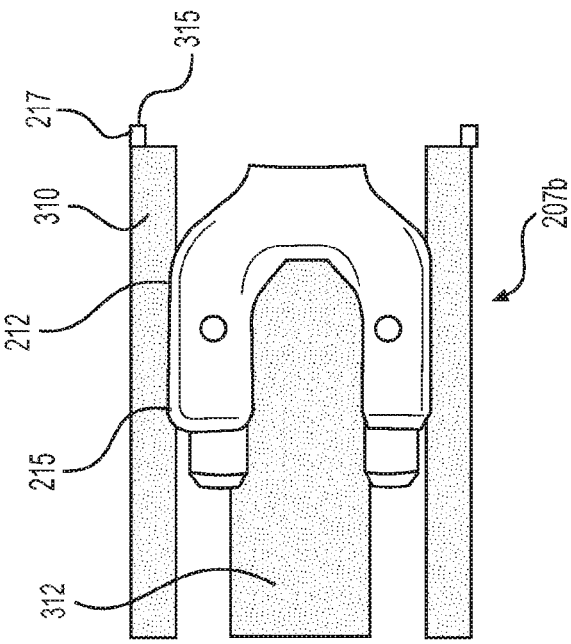
FIG. 3A
FIG. 3B

PERCUTANEOUS BONE SCREW DEVICE AND METHOD

BACKGROUND

Bone screws generally comprise an implantable screw capable of internal fixation or anchoring, and can be used to surgically correct many types of injuries or deformities including scoliosis or kyphosis. Bone screws can be used to repair a fracture, or to secure rods, plates or nails, and can be permanent, semi-permanent or bio-degradable. For example, a bone screw may be left in place after a patient heals, or the bone screw may be surgically removed.

Different types of implants (e.g., screws, pins, rods) are sometimes used in spinal surgery to help fix the spine into a more normal position and stabilize a specific area of the spinal column. For example, a cortical screw is a type of bone screw designed to screw into bony prominences of the posterior vertebra or other bone where dense cortical bone is predominantly present, whereas a cancellous bone screw, which has a different thread pattern, is sometimes used during surgery to secure the anterior vertebra or other bone where porous cancellous bone is present in greater quantity. Functioning as firm anchor points, two or more bone screws can be interconnected using locking rods, allowing a spinal segment to be fixated for stabilization or fusion.

Screws for internal fixation can be surgically inserted either open or percutaneously. If they are inserted open, the skin, muscle, and connective tissue are split and retracted surgically, providing open exposure to the underlying bone. Screws and other hardware (e.g., to interconnect the screws) are then implanted, after which the muscle and skin are re-approximated and surgically closed (using sutures or other method).

The most common method for percutaneous insertion of screws for internal fixation is the use of cannulated screws with surgical guide wires. The guide wire, which has a sharp tip that may also be threaded, is mounted to the end of a drill and surgically inserted under fluoroscopic guidance or image guidance until it penetrates through skin and muscle and anchors into bone. Small diameter (1.5 mm or less) guide wires are typically used so that they can be disengaged and repositioned without substantially damaging bone if they do not strike the bone in the desired target. Tools such as dilators, drills, and taps that are cannulated are then positioned over the anchored guide wire and forced down into contact with the bone. These tools are used to prepare the hole to accept the screw. A cannulated screw is then positioned over the guide wire and a cannulated screwdriver is used to insert the screw into bone while the guide wire stays in position. After screw insertion, the guide wire is removed and the puncture required to place the guide wire and screw is sealed.

Pins, screws, and rods can also be used for external fixation. In this case, a portion of the screws and pins reside outside of the body, but pass through the skin and muscle to connect to bone, usually at some distance from the injury or surgical region.

Whether used for internal or external fixation, percutaneous insertion and placement of a bone screw can result in tissue injury. For example, during the insertion procedure, the tap passed over the guide wire or the screw threads may become entangled with connective tissues between the entry point and a bone fixation region which may lead to trauma and/or infection. Moreover, the percutaneous placement of screws can result in the entanglement, entrapment, laceration or compression of one or more nerve fibers that may lead to severe pain, nerve palsy and/or paralysis.

In some cases, using a dilator tube through which the screw is inserted can mitigate this problem. A tube (or sequence of successively larger tubes) is inserted through muscle and connective tissue to form a channel to a position on a bone. A screw can then be passed through the tube and driven into the bone without contacting soft tissues. However, this method can be tedious and it can be difficult to introduce the tube, which must have an inside diameter adequate to pass the screw and screw head, and a substantial wall thickness for tube strength.

SUMMARY

Some embodiments of the invention include a bone screw device comprising a screw including a screw shaft, a screw head and screw tip coupled to the screw shaft. The screw shaft includes a screw thread, and a temporary encasement at least partially covering the screw. In some embodiments, the temporary encasement envelops substantially all of the screw thread. Some embodiments include a temporary encasement comprising a substantially symmetrically curved surface extending over the screw tip.

In some embodiments, the temporary encasement comprises a biocompatible material. The biocompatible material can be an osteoinductive, a hemostatic, and/or a bacteriocide. Some embodiments include a temporary encasement comprising a therapeutic, and in some embodiments, the therapeutic is dispersed within the temporary encasement. In some embodiments, the temporary encasement comprises a wax.

In some embodiments, the screw shaft further includes a proximal end and a distal end, and the screw head is substantially U-shaped and coupled to the proximal end. In some embodiments, the screw includes an extension tip comprising a shaft including a screw thread, a tip proximal end coupled to the screw distal end, and a tip distal end extending from the distal end of the shaft.

Some embodiments of the invention include a system for percutaneous implantation of a bone screw. In some embodiments, the system can include a bone screw comprising a proximal end and a distal end, a screw shaft, a screw head, and screw tip coupled to the screw shaft. The screw shaft can comprise a shaft proximal end and a distal shaft end and can include a screw thread, and a temporary encasement at least partially covering the screw. In some embodiments, the screw shaft is configured and arranged to be at least partially rotated by a screwdriver.

In some embodiments, the screw head is substantially U-shaped and coupled to the proximal shaft end, and the screwdriver is coupled to an inner surface of the screw head. Some embodiments include a sleeve at least partially surrounding the screwdriver shaft. In some embodiments, the sleeve is at least partially coupled with the temporary encasement. In some further embodiments, the sleeve is at least partially retractable away from the screw. In some embodiments, a coupling of the sleeve with the temporary encasement occurs at a transition region, and comprises a substantially smooth tubular shell at least partially surrounding the screwdriver and bone screw.

DESCRIPTION OF THE DRAWINGS

FIG. 2A illustrates a bone screw in accordance with another embodiment of the invention.

FIG. 2B illustrates an encased bone screw in accordance with another embodiment of the invention.

FIG. 3A illustrates a screwdriver shaft and bone screw assembly in accordance with at least one embodiment of the invention.

FIG. 3B illustrates a blown-up region A of the assembly of FIG. 3A in accordance with at least one embodiment of the invention.

DETAILED DESCRIPTION

Figure 1A:
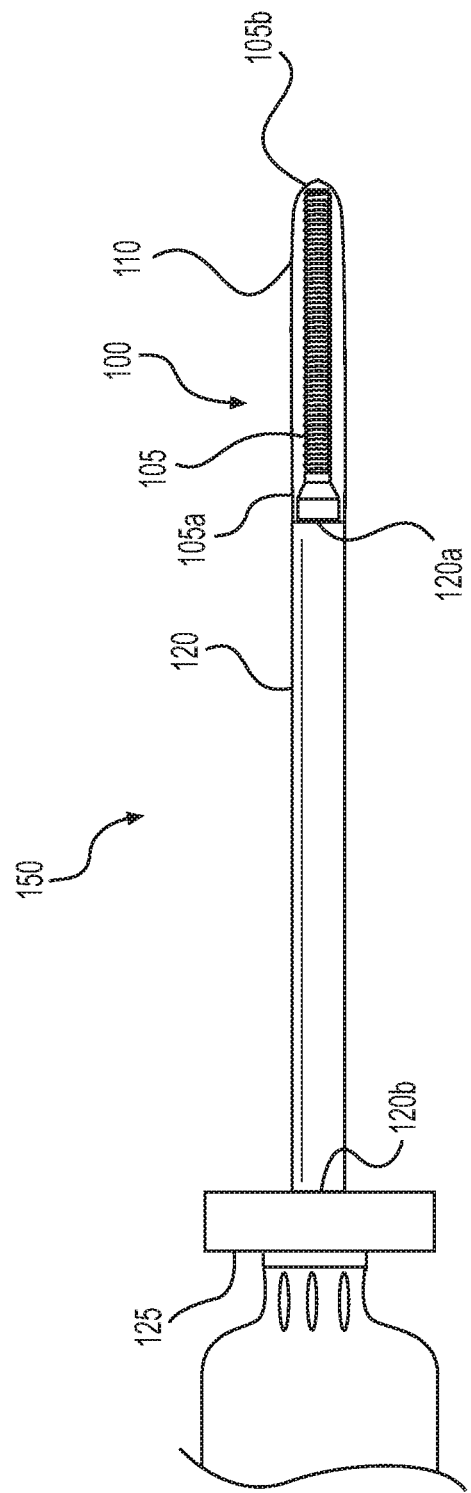
FIG. 1A illustrates a screwdriver coupling to an encased bone screw in accordance with at least one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

Figure 1B:
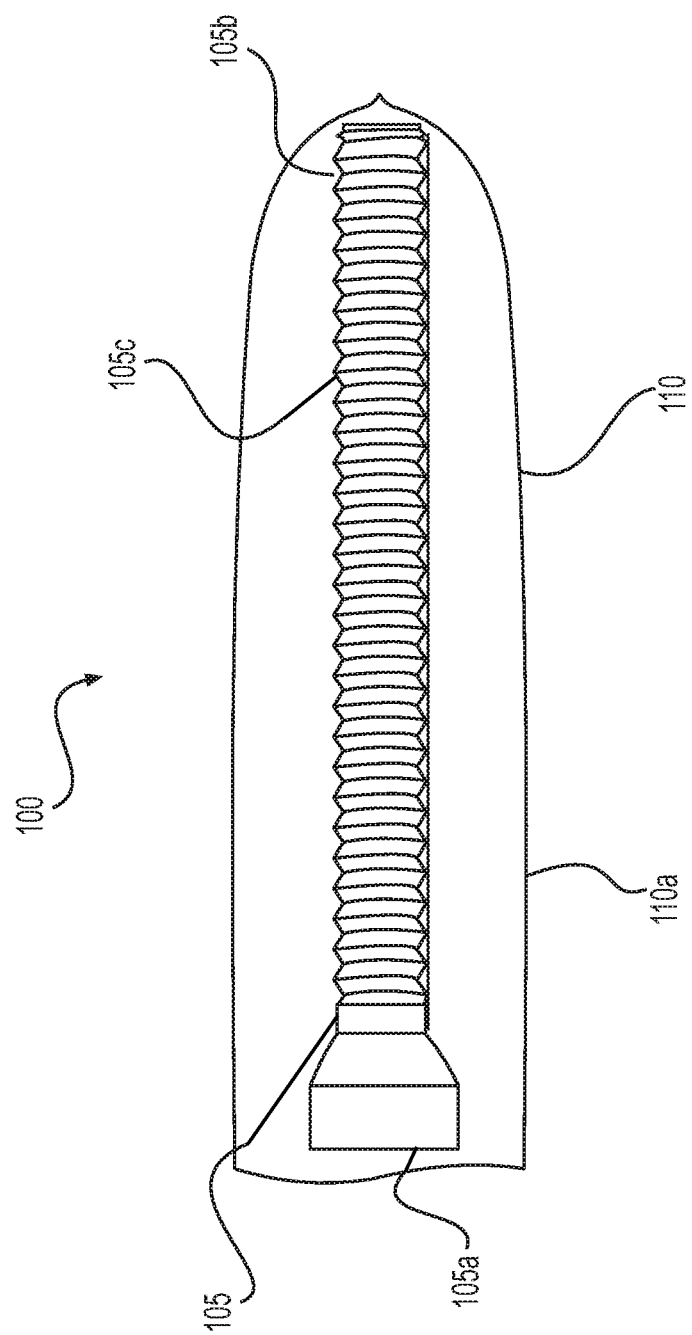
FIG. 1B illustrates an encased bone screw in accordance with at least one embodiment of the invention.

Some embodiments of the invention provide a modified bone screw 100 to ease percutaneous insertion. For example, some embodiments of the invention provide a bone screw 100 with a temporarily altered outer surface. FIG. 1A illustrates a screwdriver 150 coupling to an encased bone screw 100 in accordance with at least one embodiment of the invention, and FIG. 1B illustrates an encased bone screw 100 in accordance with a further embodiment of the invention. As shown in FIG. 1A, and in more detail in FIG. 1B, in some embodiments, the bone screw 100 can be manufactured with a temporary encasement 110 providing an encased bone screw 100. In some embodiments, the temporary encasement 110 can provide a temporarily altered outer surface surrounding the screw shaft 105 that may result in a temporarily modified length to diameter ratio. In some embodiments, the shape, symmetry and/or volume of the bone screw 100 is temporarily altered using the temporary encasement 110 covering the bone screw shaft 105 in order to at least partially reduce soft tissue interaction during insertion into a patient (e.g., when using a bone screwdriver 150).

For example, in some embodiments, the encasement 110 can be shaped to provide a spear-shaped volume around the bone screw shaft 105. In some other embodiments, the temporary encasement 110 can be shaped to provide volumes around the bone screw shaft 105 that can be rod-shaped, bullet-shaped, or knife-shaped. In some embodiments, the temporary encasement 110 can be shaped around the bone screw shaft 105 to form a volume of the bone screw 100 with a substantially symmetrically pointed curved outer surface.

As depicted in FIG. 1A, in some embodiments, a screwdriver 150 can be coupled with an encased bone screw 100. In some embodiments, the screwdriver 150 can include a screwdriver shaft 120 including a distal end 120a and a proximal end 120b. As shown, the screwdriver 150 can include a handle 125 coupled to the proximal end 120b of the shaft 120. In some embodiments, the distal end 120a of the screwdriver shaft 120 can be coupled with the screw shaft 105 at a screw head 105a. In some embodiments, a temporary encasement 110 can at least partially envelop the screw shaft 105. For example, as shown in FIG. 1B, in some embodiments, a temporary encasement 110 can at least partially envelop the screw 100 covering at least the screw shaft 105 including the screw thread 105c, the screw head 105a, and the screw tip 105b.

In some further embodiments, the temporary encasement 110 may envelop more or less of the screw 100. For example, in some embodiments, a temporary encasement 110 can at least partially envelop the screw 100 covering at least the screw shaft 105 including the screw thread 105c, and the screw tip 105b, without enveloping the screw head 105a. In other embodiments, a temporary encasement 110 can at least partially envelop the screw 100 covering at least the screw shaft 105 including the screw thread 105c, and the screw head 105a without enveloping the screw tip 105b. In some further embodiments, the temporary encasement 110 can at least partially envelop the screw thread 105c only.

In some embodiments, the thickness of the temporary encasement 110 can be substantially constant. For example, in some embodiments, the thickness of the temporary encasement 110 can form a substantially constant thickness envelope over the screw 100 covering at least the screw shaft 105 including the screw thread 105c, the screw head 105a, and the screw tip 105b. In some other embodiments, the thickness of the temporary encasement 110 may be substantially non-uniform. In some embodiments, the thickness of the temporary encasement 110 may be substantially constant over at least one region of the screw 100 but different from another region of the screw 100. In some other embodiments, the thickness of the temporary encasement 110 may be substantially non-uniform within a region of the screw 100. For example, in some embodiments, the thickness of the temporary encasement 100 may be substantially non-uniform over the screw shaft 105 including the screw thread 105c, the screw head 105a, and the screw tip 105b.

In some embodiments, the material properties of the temporary encasement 110 (including, but not limited to, the density, hardness, and brittleness) can be substantially constant. For example, in some embodiments, the material properties of the temporary encasement 110 can be substantially constant over the screw 100 covering at least the screw shaft 105 including the screw thread 105c, the screw head 105a, and the screw tip 105b. In some other embodiments, the material properties of the temporary encasement 110 may be substantially non-uniform. In some embodiments, the material properties of the temporary encasement 110 may be substantially constant over at least one region of the screw 100, but different from another region of the screw 100. In some other embodiments, the material properties of the temporary encasement 110 may be substantially non-uniform within a region of the screw 100. For example, in some embodiments, the material properties of the temporary encasement 110 may be substantially non-uniform over the screw shaft 105 including the screw thread 105c, the screw head 105a, and the screw tip 105b. In some further embodiments, the material properties of the temporary encasement 110 can be most dense, hard, and brittle at the screw tip 105b and less dense, hard, and brittle in regions of the temporary encasement enveloping other portions of the screw 100.

Figure 1C:
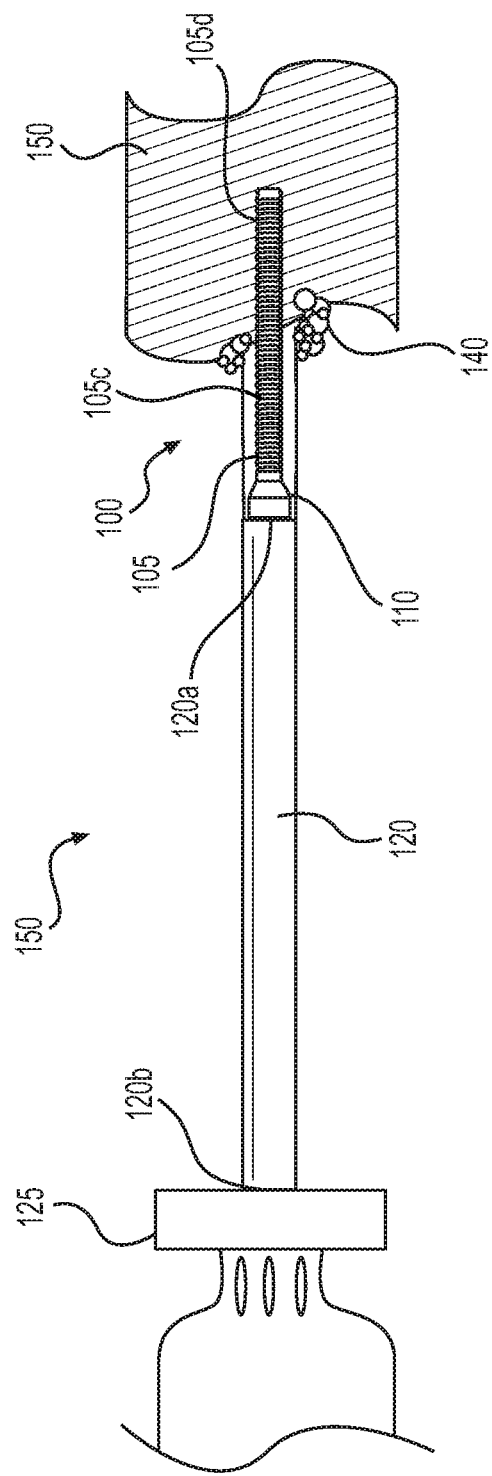
FIG. 1C illustrates an encased bone screw bone insertion in accordance with some embodiments of the invention.

In some embodiments, the temporary encasement 110 may comprise a coating that forms a smooth, substantially bullet-shaped surface over at least the screw threads 105c. In some embodiments, the temporary encasement 110 can include a substantially smooth outer surface 110a. In some embodiments, the temporary encasement 110 may have sufficient hardness to allow the bone screw 100 to penetrate through soft tissues such as muscle substantially intact, but soft and/or brittle enough to allow at least a portion of the temporary encasement 110 to crumble and/or substantially depart from one or more of the screw shaft 105, the screw thread 105c and the screw tip 105b, and the screw head 105a during penetration into bone. For example, FIG. 1C illustrates an encased bone screw 100 bone insertion in accordance with some embodiments of the invention. In some embodiments, when the screwdriver 150 is coupled with the bone screw 100 (as depicted in FIG. 1A) and driven into a patient, the temporary encasement 110 may crumble and/or extrude away as the screw penetrates bone leaving encasement debris 140. In some embodiments, substantially all the temporary encasement 110 may be stripped from any region of screw 100 that enters the bone.

In some other embodiments, the temporary encasement 110 may be at least partially removed from the screw 100 upon entering the bone (i.e., at least some fraction of the temporary encasement 110 may remain at an interface between the bone and the screw 100). In some embodiments, when the temporary encasement 110 comprises a material that comprises an osteoinductive, and/or hemostatic, and/or bacteriocidal, after driving the screw into bone, the presence of residual material (debris 140), derived from the encasement 110 in and around the screw-bone interface, may provide therapeutic value. Moreover, in some embodiments, at least some of the temporary encasement 110 may remain on the screw 100, and may provide some lubricating effect.

Some embodiments can include bone screws with alternative geometries. For example, FIG. 2A illustrates a bone screw 200 in accordance with another embodiment of the invention, and FIG. 2B illustrates the bone screw 205 (the bone screw 200 including temporary encasement 217). As shown, screws 200, 205 can be especially suited to percutaneous implantation. For example, in some embodiments, screws 200, 205 can include a leading small-diameter tip 220b that can penetrate bone and more easily hold a desired trajectory on a contoured complex surface (i.e., without wandering across the bone surface) than a standard screw tip (e.g., a screw 200 without the extension tip 220). The screws 200, 205 can then be advanced and inserted into bone, either with or without a previously drilled pilot hole. As shown, in some embodiments, the bone screws 200, 205 comprising a distal end 202a and a proximal end 202b, and the bone screw 205 comprising a distal end 207a and a proximal end 207b, can include a screw shaft 210 comprising a distal end 210a and a proximal end 210b coupled to a U-shaped screw head 212 including an inner surface 212a. In some embodiments, screws 200, 205 also comprise a screw thread 215 coupled to an extension tip 220 with tip end 220b, and a shaft 220d and a proximal end 220a. As shown, in some embodiments, the U-shaped screw head 212 is wider than the shaft 220d, as is typical for standard top-loading pedicle screws into which interconnecting rods are locked after the screw has been inserted.

In some embodiments, the tip end 220b can include a tip taper 220c, and the shaft 220d can comprise a screw thread 220e. In some embodiments, the screws 200, 205 can comprise a standard diameter between about 3.5 mm and 7 mm. In some embodiments, the shaft 220d can be between about 1 mm to about 2 mm in diameter and the tip end 220b can extend between about 2 mm and about 4 mm from the proximal end 220a. In some other embodiments, the screw 200, 205 may have a diameter greater than about 7 mm, whereas in other embodiments, the screw 200, 205 may have a diameter less than about 3.5 mm. In some embodiments, the shaft 220d may have a diameter less than about 1 mm, whereas in other embodiments, the diameter may be greater than about 2 mm. Some embodiments include a tip end 220b that can extend up to about 2 mm, whereas in other embodiments, the tip end 220b can extend further than about 4 mm from the proximal end 220a.

In some embodiments, the leading small-diameter tip 220b can penetrate bone and hold the desired trajectory on a contoured complex surface more easily (i.e., without wandering across the bone surface) than a standard screw tip (e.g., a screw 200, 205 without the extension tip 220). The screw 200, 205 can then be advanced and inserted into bone, either with or without a previously drilled pilot hole.

As shown in FIG. 2B, the bone screw 205 can include a temporary encasement 217 to aid in streamlining insertion. The wide screw head architecture illustrated by the screw head 212 can be difficult to insert percutaneously because the screw head 212 can become entangled with body matter while being driven The temporary encasement 217 can envelop the screw 205 covering at least the shaft 210, and can facilitate insertion, making it unnecessary to first insert a tubular retractor. In some embodiments as shown, the temporary encasement 217 can gradually taper toward the tip 220, ending at the distal end 210a of the shaft 210, and flaring to a larger diameter toward the head 212. In some further embodiments, the temporary encasement 217 may envelop more or less of the screw 205. For example, in some embodiments, a temporary encasement 217 can at least partially envelop the screw 205 covering at least the screw shaft 210 including the screw thread 215, and the distal end 210a. In other embodiments, the temporary encasement 217 can at least partially envelop the screw 200 covering at least the screw shaft 210 including the screw thread 215, and the screw head 212 without enveloping the inner surface 212a. In some further embodiments, the temporary encasement 217 can at least partially envelop the screw thread 215 only. In some other embodiments, the temporary encasement 217 can at least partially envelop the extension tip 220.

In some embodiments, the thickness of the temporary encasement 217 can be substantially constant. For example, in some embodiments, the thickness of the temporary encasement 217 can be a substantially constant thickness envelope over the screw 205, covering at least the screw shaft 210 including the screw thread 215, the screw head 212, and the distal end 210a. In some other embodiments, the thickness of the temporary encasement 217 may be substantially non-uniform. In some embodiments, the thickness of the temporary encasement 217 may be substantially constant over at least one region of the screw 205, but different from another region of the screw 205. In some other embodiments, the thickness of the temporary encasement 217 may be substantially non-uniform within a region of the screw 205. For example, in some embodiments, the thickness of the temporary encasement 217 may be substantially non-uniform over the screw shaft 210, including the screw thread 215, the screw head 212, and the distal end 210a.

In some embodiments, the material properties, including but not limited to density, brittleness, and hardness, of the temporary encasement 217 can be substantially constant. For example, in some embodiments, the density of the temporary encasement 217 can be substantially constant over the screw 205, covering at least the screw shaft 210 including the screw thread 215, the screw head 212, and the distal end 210a. In some other embodiments, the density of the temporary encasement 217 may be substantially non-uniform. In some embodiments, the density of the temporary encasement 217 may be substantially constant over at least one region of the screw 205, but different from another region of the screw 205. In some other embodiments, the density of the temporary encasement 217 may be substantially non-uniform within a region of the screw 205. For example, in some embodiments, the density of the temporary encasement 217 may be substantially non-uniform over the screw shaft 210 including the screw thread 215, the screw head 212, and the distal end 210a. In some embodiments, the density of the temporary encasement 217 is most dense at the screw tip and less dense in other portions of the screw 205.

In some embodiments, the temporary encasement 110, 217 can comprise a wax. In some embodiments, the temporary encasement 110, 217 may be soft and/or brittle enough that the temporary encasement 110, 217 crumbles away as the screw penetrates bone. In some embodiments, the temporary encasement 110, 217 can comprise a material that is biocompatible, osteoinductive, and/or hemostatic, and/or bacteriocidal. Further, in some embodiments, a therapeutic compound may be dispersed within the temporary encasement 110, 217, or the temporary encasement 110, 217 may comprise a therapeutic compound.

In some embodiments, the wax can comprise a hydrocarbon-based wax. Some embodiments include wax comprising an ester of a monohydric long-chain fatty alcohol and a long chain fatty acid. In some embodiments, the temporary encasement 110, 217 can comprise natural waxes, including, but not limited to animal-derived waxes such as lanoline, spermaceti wax, and wool fat, insect waxes such as bees wax, and vegetable-derived wax such as candelila wax, carnauba wax or castor wax. In some other embodiments, the temporary encasement 110, 217 can comprise a synthetic wax. For example, some embodiments can include polyethylene glycol-based wax, hydrogenated or partially hydrogenated vegetable oil based wax. Some embodiments of the invention include a temporary encasement 110, 217 comprising at least one biocompatible wax. For example, some embodiments can include at least biodegradable or bioabsorbable wax. Some embodiments include a temporary encasement 110, 217 comprising a non-waxy biocompatible semi-crystalline or amorphous polymer.

In some embodiments, the temporary encasement 110, 217 includes a coating with a melting temperature of about 98° F. (i.e., body temperature). In some other embodiments, the temporary encasement 110, 217 includes a coating with a melting temperature greater than 98° F., whereas in other embodiments, the temporary encasement 110, 217 includes a coating with a melting temperature of less than 98° F. In some embodiments, the temporary encasement 110, 217 comprises a material with a melting or softening point that is selected based on the length of time of the procedure. For example, in some embodiments, the temporary encasement 110, 217 comprises a material that is substantially solid at room temperature prior to entering patient, but later becomes softer and/or enters a melting phase as its temperature is raised by the body of the patient during the procedure. In some embodiments, the temporary encasement 110, 217 comprises a material that is substantially solid at room temperature prior to entering the patient and during percutaneous insertion, but becomes softer and/or enters a melting phase as its temperature is raised as the bone screw 100 enters the bone of the patient.

In some embodiments of the invention, the bone screw 100, 200, 205 can comprise a biocompatible metal. In some embodiments, the biocompatible metal can be stainless steel, such as a surgical stainless steel. In other embodiments, other metals or metal alloys can be used based on at least one of iron, chromium, nickel, molybdenum, titanium or other group IV metal. In other embodiments, the bone screw 100, 200, 205 can comprise a polymer, a ceramic, a glass, a metal-matrix composite, or combinations thereof.

FIG. 3A illustrates a screwdriver 300 and bone screw 200 assembly in accordance with at least one embodiment of the invention, and FIG. 3B illustrates a blown-up region A of the assembly of FIG. 3A in accordance with at least one embodiment of the invention. FIG. 3B shows shaft 312 coupled with the inner surface 212a of the screw head 212. In some embodiments, the shaft 312 can pass through a plastic or metal sleeve 310. In some embodiments, the plastic or metal sleeve 310 can couple with the temporary encasement 217 at a transition region 315 to form a smooth tubular shell surrounding the screwdriver 300 and bone screw 205. In some embodiments, the plastic or metal sleeve 310 is at least partially retractable away from the bone screw 200 and the transition region 315.

In some embodiments, any one of the bone screws 100, 105, 200, 205 described above and illustrated in FIGS. 1A-1C, 2A-2B, and 3A-3B may be driven by a medically qualified individual such as a surgeon, physician, or a physician assistant. In some further embodiments, any one of the bone screws 100, 105, 200, 205 described above and illustrated in FIGS. 1A-1C, 2A-2B, and 3A-3B may be driven by a surgical robot (and optionally an imaging system) that utilizes a Cartesian positioning system that allows movement of a surgical instrument to be individually controlled in an x-axis, y-axis and z-axis. A surgical robot suitable for this task has been described in U.S. Provisional Patent Application No. 61/662,702 filed on Jun. 21, 2012, U.S. Provisional Patent Application No. 61/800,527 filed on Mar. 15, 2013, and Non-Provisional patent application Ser. No. 13/924,505 filed on Jun. 21, 2013, the entire contents of which are hereby incorporated by reference. As described, the surgical robot can include a base, a robot arm coupled to and configured for articulation relative to the base, as well as an end-effectuator coupled to a distal end of the robot arm. The effectuator element can include the surgical instrument or can be configured for operative coupling to the surgical instrument, and the roll, pitch and yaw rotation of the end-effectuator and/or surgical instrument to be controlled without creating movement along the x-axis, y-axis, or z-axis. The system can be configured to automatically position and rigidly hold the end-effectuator and/or the surgical instrument in accurate alignment with a required trajectory, such as, for example, a selected trajectory of a pedicle screw during pedicle screw insertion procedures. In case of movement of the patient, the system can be configured to automatically adjust the position of the robot to maintain desired alignment relative to an anatomical region of interest.

In some embodiments, when the screwdriver 300 is coupled with the bone screw 205 (as depicted in FIG. 3A) and driven into a patient, the temporary encasement 217 may crumble and/or extrude away as the screw 205 penetrates bone leaving encasement debris (illustrated by 140 in FIG. 1C). In some embodiments, substantially all the temporary encasement 217 may be stripped from any region of screw 205 that enters the bone. In some other embodiments, the temporary encasement 217 may be at least partially removed from the screw 205 upon entering the bone. In some embodiments, when the temporary encasement 217 comprises a material that comprises an osteoinductive, and/or hemostatic, and/or bacteriocidal, after driving the screw 205 into bone, the presence of residual material (debris 140), derived from the encasement 217 in and around the screw-bone interface, may provide therapeutic value. In some embodiments, some of the temporary encasement 217 remains on the screw 205 and provides some lubricating effect.

In some embodiments, any one of the bone screws 100, 200, 205 described above and illustrated in FIGS. 1A-1C, 2A-2B, and 3A-3B can be used for therapy within any one of the cervical region of the human spine, the thoracic region of the human spine, the lumbar region of the human spine, and the sacral region of the human spine.

As described earlier, in some embodiments, when any one of the bone screws 100, 200, 205 described above and illustrated in FIGS. 1A-1C, 2A-2B, and 3A-3B is turned and driven into bone, the temporary encasement 110, 217 can be at least partially shed (i.e., the material may at least partially crumble, if the material is brittle, or the material may at least partially flow if material is softening or entering a melting phase). In some other embodiments, the temporary encasement 110, 217 can be removed by thermal-induced melting and/or softening. For example, in some embodiments a conventional heating element can be included in the screwdriver 150, 300 just proximal to the screw 100, 205 to heat the screw 100, 205 to induce melting and/or softening of the temporary encasement 110, 217 on the screw 100, 205. In some other embodiments, an electrical current can be used to heat the screw 100, 205 to induce melting and/or softening of the temporary encasement 110, 217 on the screw 100, 205.

Some other embodiments can include chemically-induced removal of the temporary encasement 110, 217. For example, some embodiments can include injection of a chemical through a cannulation in a shaft of the screwdriver 150, 300, and/or fenestrations or porosity in the screw 100, 200, 205. In some embodiments, the chemical may at least partially dissolve and/or penetrate at least some fraction of the temporary encasement 110, 217. In some other embodiments, the chemical may at least partially react with at least some fraction of the temporary encasement 110, 217. In some embodiments, the chemical may soften the temporary encasement 110, 217. In some embodiments, contact between any fraction of the temporary encasement 110, 217 may cause the temporary encasement 110, 217 to at least partially separate from the screw 100, 200, 205.

The invention claimed is:

1. A bone screw device comprising:
    a screw comprising a screw shaft, a screw head and screw tip coupled to the screw shaft,
    the screw shaft including a screw thread; and
    a temporary encasement at least partially covering the screw, wherein the temporary encasement crumbles or extrudes away from the screw during penetration into bone, thereby leaving encasement debris and the screw with at least a portion of the temporary encasement removed.

2. The bone screw device of claim 1, wherein the temporary encasement envelops substantially all of the screw thread.

3. The bone screw device of claim 2, wherein the temporary encasement comprises a substantially symmetrically curved surface extending over the screw tip.

4. The bone screw device of claim 1, wherein the temporary encasement comprises a biocompatible material.

5. The bone screw device of claim 4, wherein the biocompatible material is at least one of an osteoinductive, a hemostatic and a bacteriocide.

6. The bone screw device of claim 1, wherein the temporary encasement comprises a therapeutic compound.

7. The bone screw device of claim 6, wherein the therapeutic compound is dispersed within the temporary encasement.

8. The bone screw device of claim 1, wherein the temporary encasement comprises a wax.

9. The bone screw device of claim 1, wherein the screw shaft further includes: a shaft proximal end and a shaft distal end; and wherein the screw head is substantially U-shaped and coupled to the shaft proximal end.

10. The bone screw device of claim 9, further comprising: an extension tip comprising a tip shaft including a screw thread, and a tip proximal end coupled to the bone screw distal end, and a tip end extending from the shaft distal from the bone screw distal end.

11. A system for percutaneous implantation of a bone screw, comprising:
    a screwdriver having a sleeve and a shaft passing through the sleeve;
    a bone screw comprising a proximal end and a distal end and including a screw shaft, a screw head, and a screw tip coupled to the screw shaft,
    the screw shaft comprising a proximal shaft end and a distal shaft end and including a screw thread; and
    a temporary encasement at least partially covering the screw;
    wherein the screw shaft is configured and arranged to be at least partially rotated within the sleeve by the screwdriver, and
    wherein the temporary encasement crumbles or extrudes away from the bone screw during penetration into bone, thereby leaving encasement debris and the bone screw with at least a portion of the temporary encasement removed.

12. The system of claim 11, wherein the screw head is substantially U-shaped and coupled to the proximal screw shaft end; and wherein the screwdriver is coupled to an inner surface of the screw head.

13. The system of claim 11, wherein the sleeve is a substantially rigid sleeve at least partially surrounding the screwdriver shaft.

14. The system of claim 13, wherein the sleeve is at least partially coupled with the temporary encasement.

15. The system of claim 11, wherein the sleeve is at least partially retractable away from the screw.

16. The system of claim 14, wherein the coupling of the sleeve with the temporary encasement occurs at a transition region and comprises a substantially smooth tubular shell at least partially surrounding the screwdriver and bone screw.

17. The bone screw device of claim 11, wherein the temporary encasement comprises a biocompatible material.

18. The bone screw device of claim 17, wherein the biocompatible material is at least one of an osteoinductive, a hemostatic and a bacteriocide.

19. The bone screw device of claim 17, wherein the biocompatible material comprises a therapeutic compound.

20. The bone screw device of claim 17, wherein the biocompatible material comprises a wax.

* * * * *